(12) United States Patent
McGuire, Jr. et al.

(10) Patent No.: US 11,389,303 B1
(45) Date of Patent: Jul. 19, 2022

(54) EXTERNALLY THREADED EXPANDABLE ORTHOPEDIC IMPLANT

(71) Applicant: Zavation Medical Products, LLC, Flowood, MS (US)

(72) Inventors: Robert Alton McGuire, Jr., Ridgeland, MS (US); Joseph Matthew Jones, Madison, MS (US); John Lawrence Walker, Madison, MS (US)

(73) Assignee: Zavation Medical Products, LLC, Flowood, MS (US)

( * ) Notice: Subject to any disclaimer, the term of this patent is extended or adjusted under 35 U.S.C. 154(b) by 0 days.

(21) Appl. No.: 17/496,081

(22) Filed: Oct. 7, 2021

(51) Int. Cl.
| | |
|---|---|
| *A61F 2/44* | (2006.01) |
| *A61F 2/46* | (2006.01) |
| *A61F 2/30* | (2006.01) |
| *A61B 17/70* | (2006.01) |

(52) U.S. Cl.
CPC ........ *A61F 2/4455* (2013.01); *A61B 17/7001* (2013.01); *A61F 2/30771* (2013.01); *A61F 2/4611* (2013.01); *A61F 2002/30266* (2013.01); *A61F 2002/30579* (2013.01); *A61F 2002/30774* (2013.01); *A61F 2002/30886* (2013.01)

(58) Field of Classification Search
CPC .. A61F 2/4455; A61F 2/4611; A61F 2/30771; A61F 2/44; A61F 2/442; A61F 2002/30266; A61F 2002/30579; A61F 2002/30774; A61F 2002/30886; A61B 17/7001
USPC ....................... 623/17.15–17.16; 606/99–100
See application file for complete search history.

(56) References Cited

U.S. PATENT DOCUMENTS

| | | | | |
|---|---|---|---|---|
| 5,776,196 | A | * | 7/1998 | Matsuzaki ............ A61L 31/022 623/17.16 |
| 5,885,287 | A | * | 3/1999 | Bagby ...................... A61F 2/44 623/16.11 |
| 6,176,882 | B1 | | 1/2001 | Biedermann et al. |
| 6,217,579 | B1 | * | 4/2001 | Koros ................. A61F 2/30744 623/17.11 |
| 6,436,142 | B1 | * | 8/2002 | Paes ...................... A61F 2/4611 623/17.15 |
| 6,451,057 | B1 | * | 9/2002 | Chen ...................... A61F 2/446 623/17.15 |
| 6,500,205 | B1 | | 12/2002 | Michelson |
| 7,128,760 | B2 | | 10/2006 | Michelson |
| 7,655,046 | B2 | * | 2/2010 | Dryer .................... A61F 2/4611 623/17.15 |
| 7,850,733 | B2 | | 12/2010 | Baynham et al. |

(Continued)

FOREIGN PATENT DOCUMENTS

WO      2016178078 A1      11/2016

*Primary Examiner* — Jessica Weiss
(74) *Attorney, Agent, or Firm* — IP & T Group LLP (57) ABSTRACT

An expandable screw for orthopedic insertion and expansion between a collapsed state and an expanded state. The screw has an upper externally-threaded body segment, a lower externally-threaded body segment opposite the upper external thread segments, and an expansion member extending along a longitudinal axis thereof. The expansion member connecting the upper externally-threaded body segment to the lower externally-threaded body segment, and configured during the expansion between the collapsed state and the expanded state to separate the upper externally-threaded body segment from the lower externally-threaded body segment.

21 Claims, 8 Drawing Sheets

(56) References Cited

U.S. PATENT DOCUMENTS

| | | | |
|---|---|---|---|
| 8,062,375 B2 | 11/2011 | Glerum et al. |
| 8,105,382 B2 | 1/2012 | Olmos et al. |
| 8,241,360 B2 | 8/2012 | Bao et al. |
| 8,535,380 B2 | 9/2013 | Greenhalgh et al. |
| 8,679,183 B2 | 3/2014 | Glerum et al. |
| 8,894,712 B2 | 11/2014 | Varela |
| 9,155,628 B2 | 10/2015 | Glerum et al. |
| 9,233,007 B2 | 1/2016 | Sungarian et al. |
| 9,320,610 B2 | 4/2016 | Alheidt et al. |
| 9,370,434 B2 | 6/2016 | Weiman |
| 9,402,737 B2 | 8/2016 | Hawkins et al. |
| 9,402,739 B2 | 8/2016 | Weiman et al. |
| 9,414,936 B2 | 8/2016 | Miller et al. |
| 9,492,288 B2 | 11/2016 | Wagner et al. |
| 9,522,070 B2 | 12/2016 | Flower et al. |
| 9,526,627 B2 | 12/2016 | Tabor et al. |
| 9,539,108 B2 | 1/2017 | Glerum et al. |
| 9,549,824 B2 * | 1/2017 | McAfee | A61F 2/442 623/17.15 |
| 9,585,766 B2 | 3/2017 | Robinson |
| 9,717,601 B2 | 8/2017 | Miller |
| 9,717,605 B2 | 8/2017 | Baynham |
| 9,757,249 B2 | 9/2017 | Radcliffe et al. |
| 9,770,343 B2 | 9/2017 | Weiman |
| 9,782,265 B2 | 10/2017 | Weiman et al. |
| 9,782,271 B2 | 10/2017 | Cipoletti et al. |
| 9,788,971 B1 | 10/2017 | Stein |
| 9,801,733 B2 | 10/2017 | Wolters et al. |
| 9,801,734 B1 | 10/2017 | Stein et al. |
| 10,278,830 B1 | 5/2019 | Walker et al. |
| 10,350,081 B2 | 7/2019 | Seifert et al. |
| 10,383,741 B2 | 8/2019 | Butler et al. |
| 10,492,924 B2 | 12/2019 | Stein et al. |
| 11,051,949 B2 | 7/2021 | Walker et al. |
| 11,173,044 B1 * | 11/2021 | Jones | A61F 2/447 623/17.15 |
| 2002/0161444 A1 * | 10/2002 | Choi | A61F 2/446 623/17.11 |
| 2011/0319997 A1 | 12/2011 | Glerum et al. |
| 2012/0265309 A1 | 10/2012 | Glerum et al. |
| 2013/0023994 A1 | 1/2013 | Glerum |
| 2013/0158669 A1 | 6/2013 | Sungarian et al. |
| 2014/0067071 A1 | 3/2014 | Weiman et al. |
| 2014/0180421 A1 | 6/2014 | Glerum et al. |
| 2016/0045328 A1 | 2/2016 | Matthews et al. |
| 2016/0081814 A1 | 3/2016 | Baynham |
| 2016/0151168 A1 | 6/2016 | Weiman et al. |
| 2016/0256291 A1 | 9/2016 | Miller |
| 2017/0056197 A1 | 3/2017 | Weiman et al. |
| 2017/0258605 A1 | 9/2017 | Blain et al. |
| 2020/0297507 A1 | 9/2020 | Iott et al. |

* cited by examiner

EXTERNALLY THREADED EXPANDABLE ORTHOPEDIC IMPLANT

CROSS REFERENCE TO RELATED APPLICATIONS

This application is related to U.S. Pat. No. 10,278,830, entitled Expandable Orthopedic Implant, filed Sep. 19, 2018, the entire contents of which are incorporated herein by reference. This application is related to U.S. Ser. No. 17/235, 587, entitled Improved-Expanding Orthopedic Implant, filed Sep. 19, 2021, the entire contents of which are incorporated herein by reference.

BACKGROUND OF THE INVENTION

Field of the Invention

The present invention relates to implant devices for treating in particular spinal disorders.

Description of the Related Art

Disorders of the bone include disorders such as for example degenerative disc disease, disc herniation, osteoporosis, spondylolisthesis, stenosis, scoliosis (and other curvature abnormalities), kyphosis, tumor, fracture, arthritis, calcification, etc. Such disorders may result from factors including trauma, disease and degenerative conditions caused by injury and aging.

Bone disorders typically result in symptoms including pain, nerve damage, and partial or complete loss of mobility. Additionally, severe pain and discomfort can occur due to the pressure exerted by bones on nerves.

In the field of medical implant devices, implant devices are often used in a collapsed state and expanded to a desired height. The following provides a non-exhaustive list of expansion devices known in the art.

U.S. Pat. No. 6,500,205 (the entire contents of which are incorporated herein by reference) describes a threaded implant having arcuate portions of upper and lower members that in a first, collapsed, or insertion position are parallel to one another and form at least a portion of a cylinder along a substantial portion of the length of the implant.

U.S. Pat. No. 7,128,760 (the entire contents of which are incorporated herein by reference) describes interbody spinal fusion implants being at least in part radially expandable at one of the leading or trailing ends to expand both the height and at least a portion of the width of the implants.

U.S. Pat. No. 7,655,046 (the entire contents of which are incorporated herein by reference) describes an expandable spinal implant comprising a cage body including at least two movable branches having first end portions that are interconnected to one another and second end portions that are movable relative to one another. An expansion member in the '046 patent co-acts with first and second shell portions to transition the cage body to an expanded configuration as the expansion member is axially displaced along said first and second pairs of longitudinal edges.

U.S. Pat. No. 8,241,360 (the entire contents of which are incorporated herein by reference) describes an artificial disc device for replacing a damaged nucleus in which the device may be inserted into the natural annulus in a collapsed or compressed state or arrangement and then may be expanded within and retained by the annulus therein.

U.S. Pat. No. 8,535,380 (the entire contents of which are incorporated herein by reference) describes an implantable orthopedic stability device. The device had a contracted and an expanded configuration which could support and be fixed to either or both of adjacent vertebrae.

U.S. Pat. No. 8,894,712 (the entire contents of which are incorporated herein by reference) describes an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member from the inferior member.

U.S. Pat. No. 8,679,183 (the entire contents of which are incorporated herein by reference) describes an expandable fusion device capable of being installed inside an intervertebral disc space to maintain normal disc spacing and restore spinal stability.

U.S. Pat. No. 9,320,610 (the entire contents of which are incorporated herein by reference) describes an expandable implant including top and bottom plates having angled inner surface that interact with expansion members. The expansion members of the '610 patent were situated on an actuator and included at least one vertical projection for interacting with a recess in the plates.

U.S. Pat. No. 9,414,936 (the entire contents of which are incorporated herein by reference) describes an intervertebral implant comprising a first component and a second component. The second component included an actuator and a third component comprises a first ramp and a second ramp axially spaced apart from the first ramp. The third component comprised rails including at least a portion of the ramps. The actuator was engageable with the third component to effect axial translation such that the ramps engage at least one of the components between a first configuration and a second configuration.

U.S. Pat. No. 9,526,627 (the entire contents of which are incorporated herein by reference) describes an intervertebral implant to be implanted within an intervertebral space between endplates of adjacent vertebra during use.

U.S. Pat. No. 9,717,601 (the entire contents of which are incorporated herein by reference) describes an implant including a first plate and a second plate, a first wedge member and a second wedge member spaced from the first wedge member that couple the first and second plates together.

U.S. Pat. No. 9,717,605 (the entire contents of which are incorporated herein by reference) describes a spinal fusion device that is expandable. The spinal fusion device of the '605 patent features a top and bottom surface for engaging adjacent vertebrae, a hollow center for stacking of bone or bone growth material, and a slidable mechanism with grooves for expanding or un-expanding the device.

U.S. Pat. No. 9,770,343 (the entire contents of which are incorporated herein by reference) describes a spacer for separating bones of a joint, the spacer includes a frame having a longitudinal axis, and ramped surfaces. In the '343 patent, an endplate configured to engage a bone of the joint had ramped surfaces mateable with the ramped surfaces of the frame. When the endplate was moved relative to the frame in a direction along the longitudinal axis of the frame, the endplate was moved in a direction away from the frame to increase the height of the spacer.

U.S. Pat. No. 9,788,971 (the entire contents of which are incorporated herein by reference) describes an expandable spinal fusion implant comprising first and second endplates coupled to an expansion member that sits within a housing.

U.S. Pat. No. 10,350,081 (the entire contents of which are incorporated herein by reference) describes an orthopedic device for a patient comprising: a spacer comprising: a body member; a translation member received in the body member, the translation member including at least one upper ramp portion and one lower ramp portion; an upper endplate having an upper contact surface for engaging a first vertebra and at least one lower ramp for engaging the upper ramp portion of the translation member, wherein the upper endplate includes an upper plate portion comprising a bottom post; a lower endplate having a lower contact surface for engaging a second vertebra and at least one upper ramp for engaging the lower ramp portion of the translation member.

U.S. Pat. No. 10,383,741 (the entire contents of which are incorporated herein by reference) describes an expandable implant including a top support assembly defining an upper surface configured to engage a first portion of vertebral bone; a bottom support assembly defining a lower surface configured to engage a second portion of vertebral bone; and a control assembly coupled to the top support assembly and the bottom support assembly and configured to control relative movement between the top support assembly and the bottom support assembly between a collapsed position and an expanded position.

U.S. Pat. No. 10,492,924 (the entire contents of which are incorporated herein by reference) describes an expandable spinal fusion implant including a housing, upper and lower endplates, a wedge positioned within the housing and between the upper and lower endplates and a drive mechanism to urge the wedge distally between the upper and lower endplates to increase the separation between the endplates and expand the overall height of the distal end of the implant.

U.S. Pat. No. 2020/0297507 (the entire contents of which are incorporated herein by reference) describes a joint spacer for therapeutically maintaining a separation of bones of a joint. The joint spacer comprises a frame having distal and proximal ends defining a longitudinal axis extending therebetween, a carriage slideably retained within the frame, an actuator screw threadably engaged with the frame, whereby when the carriage is slideably moveable by rotation of the actuator screw, an endplate ramped surface slides against a carriage ramped surface to cause the endplate to move along an axis transverse to the longitudinal axis to increase a height of the spacer.

SUMMARY OF THE INVENTION

In one embodiment, there is provided an expandable screw for orthopedic insertion and expansion between a collapsed state and an expanded state. The screw has an upper externally-threaded body segment, a lower externally-threaded body segment opposite the upper external thread segments, and an expansion member extending along a longitudinal axis thereof. The expansion member connecting the upper externally-threaded body segment to the lower externally-threaded body segment, and configured during the expansion between the collapsed state and the expanded state to separate the upper externally-threaded body segment from the lower externally-threaded body segment.

In one embodiment, there is provided a system for orthopedic insertion and expansion of an expandable screw into a bone segment of a patient, the system comprising an expandable screw, and an insertion tool which is configured to connect to the screw for actuation and expansion of the screw.

In one embodiment, there is provided a method for orthopedic insertion and expansion of an expandable screw into a bone segment of a patient, comprising inserting an expandable screw into the bone segment; and expanding the expandable screw.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

FIG. 5 is a schematic depiction of the individual components of the expandable screw with attention on the dovetail groove assembly construction;

DETAILED DESCRIPTION OF THE INVENTION

Expandable Screw Devices of the Invention

In one embodiment of the invention, as noted above, there is provided an expandable screw 10 for orthopedic insertion and expansion into a bone segment of a patient, although this invention is not limited to this specific target use.

Figure 1:
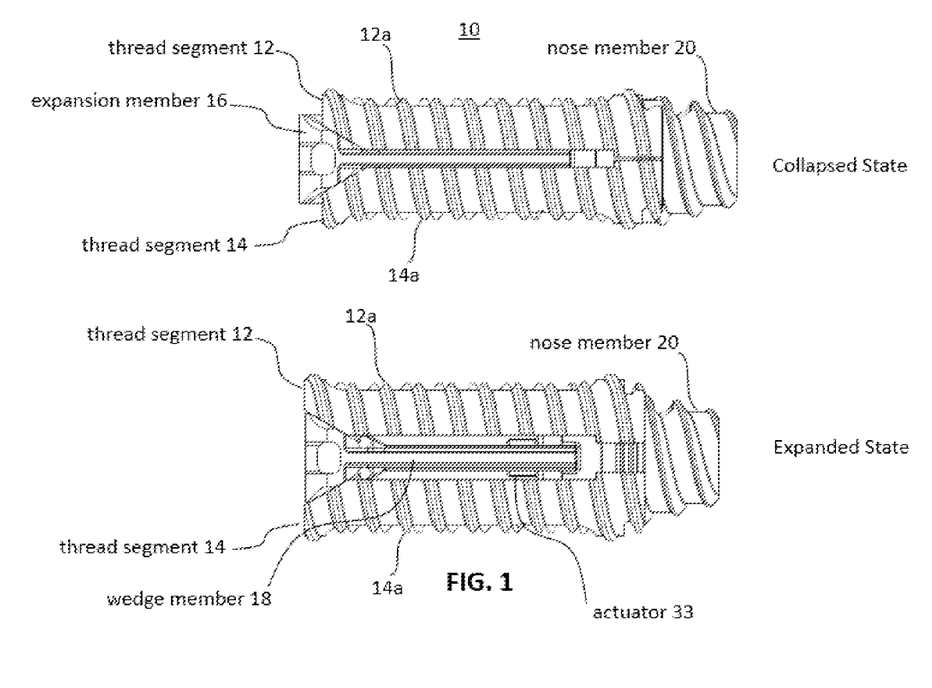
FIG. 1 is a side view of an expandable screw in a collapsed state and in an expanded state.

With reference to FIG. 1, FIG. 1 is a perspective view of the expandable screw 10 in a collapsed state and in an expanded state. In one embodiment of the invention and as shown in FIG. 1, expandable screw 10 has an upper externally-threaded body segment 12, a lower externally-threaded body segment 14 opposite the upper external thread segments 12, and an expansion member 16 extending along a longitudinal axis thereof. Expansion member 16 connects the upper externally-threaded body segment 12 to the lower externally-threaded body segment 14. (Details of connecting expansion member 16 to the upper externally-threaded body segment 12 to the lower externally-threaded body segment 14 and to nose member 20 are provided below.) Expansion member 16 is configured (during the expansion between the collapsed state and the expanded state) to separate the upper externally-threaded body segment 12 from the lower externally-threaded body segment 14. In one embodiment, in the collapsed state, the threads on the nose member and the threads on the expansion members match-up or align with each other. In one embodiment, the threads on the nose member and the threads on the expansion members have the same pitch. When the expandable screw is made, the ends of the threads on the expansion members are formed (made to start) at the point where the thread on the nose member would end. That is the starting point for the thread machining on each component is defined/controlled relative to a common datum, such that the component threads will be aligned and form a uniform screw thread when assembled.

Figure 2:
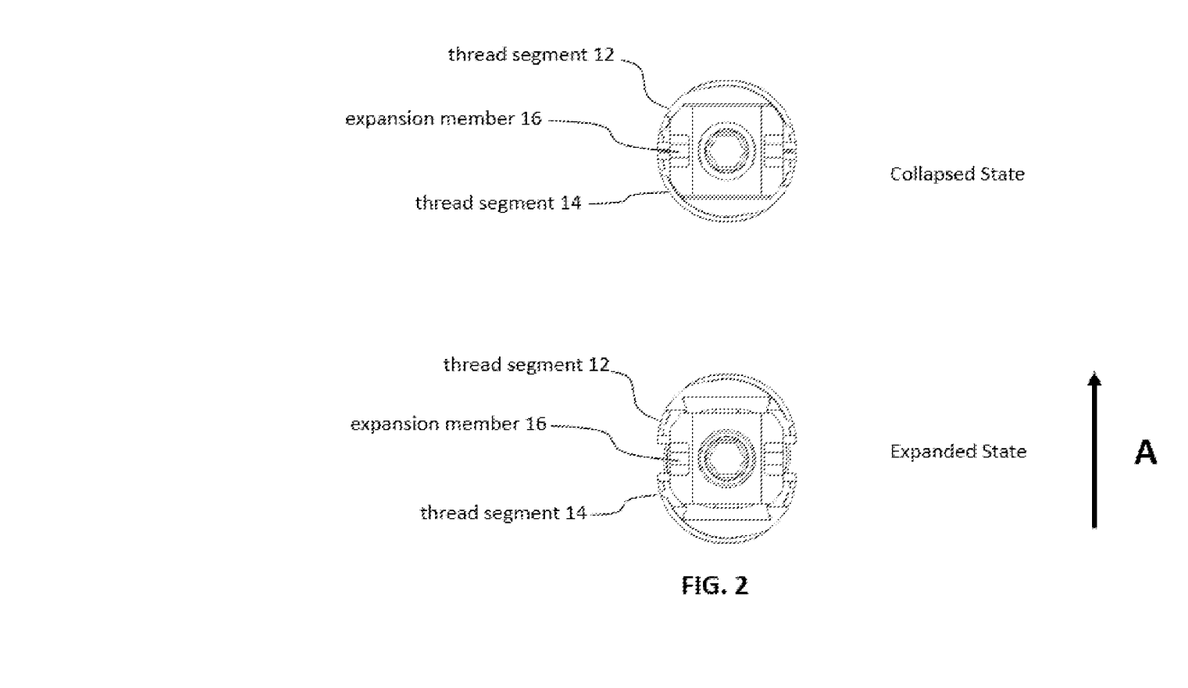
FIG. 2 is an end view of the expandable screw of FIG. 1.
Figure 3:
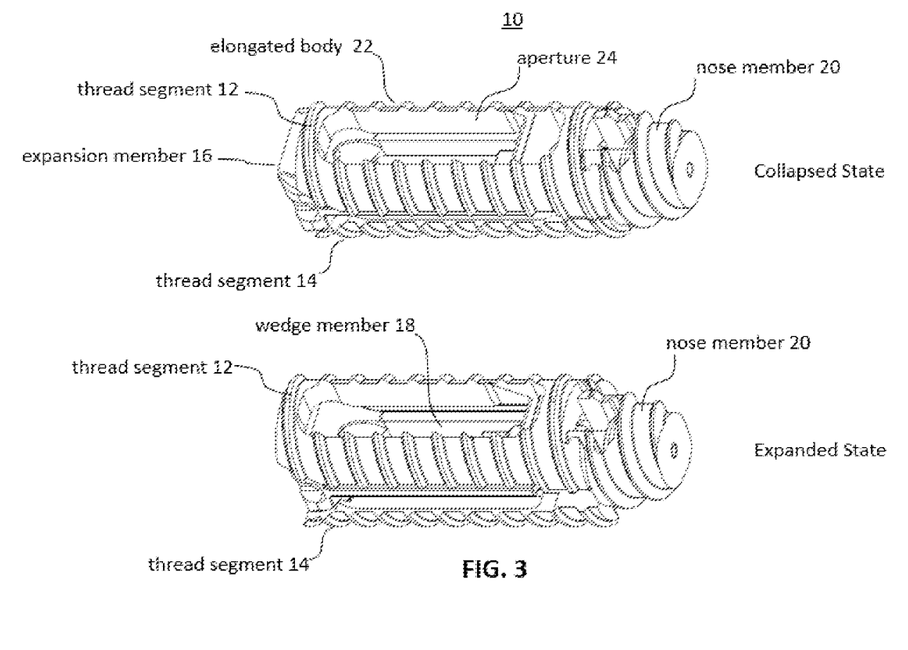
FIG. 3 is a perspective view of the of the expandable screw in the collapsed state and in the expanded state.

FIG. 2 is an end view of the expandable screw 10 showing the collapsed state and the expanded state. FIG. 2 shows expansion member 16 expanding the upper externally-threaded body segment 12 from the lower externally-threaded body segment 14 in a single expansion direction A. Accordingly, in one embodiment, screw 10 expands in a substantially single direction of motion, the deviations therefrom depending on the mechanical tolerances of the expansion member and its mechanical connections to the upper externally-threaded body segment 12 from the lower externally-threaded body segment 14. As used herein, "in a single expansion direction" means movement in one direction with only minor deviations from the expansion directions due to mechanical tolerances of the expansion member and its mechanical connections to the upper externally-threaded body segment 12 from the lower externally-threaded body segment 14.

Additionally, in one embodiment. the expansion member 16 can expand the upper externally-threaded body segment 12 from the lower externally-threaded body segment 14 in a single expansion direction without a radial deflection of the upper externally-threaded body segment 12 from the lower externally-threaded body segment 14. Accordingly, in one embodiment, screw 10 expands without a radial deflection of the upper externally-threaded body segment 12 from the lower externally-threaded body segment 14. Similar to that noted above, as used herein, "without radial deflection" means that, upon movement between the collapsed state and the expanded state, there are only minor radial deflection due to mechanical tolerances of the expansion member and its mechanical connections to the upper externally-threaded body segment 12 from the lower externally-threaded body segment 14.

In another embodiment, the expansion member 16 can expand the upper externally-threaded body segment 12 from the lower externally-threaded body segment 14 while the upper externally-threaded body segment 12 and the lower externally-threaded body segment 14 remain in a substantially fixed orientation relative to each other. Similar to that noted above, as used herein, "remains in a substantially fixed orientation" means that, upon movement between the collapsed state and the expanded state, there are only minor deviations from the relative orientation of the upper externally-threaded body segment 12 to the lower externally-threaded body segment 14 due to mechanical tolerances of the expansion member and its mechanical connections to the upper externally-threaded body segment 12 from the lower externally-threaded body segment 14.

As seen in FIG. 1, the upper externally-threaded body segment 12 and the lower externally-threaded body segment 14 in one embodiment can include threads 12a, 14a. Threads 12a and 14a are for securing the expandable screw 10 to a bone segment of a patient. Thread 12a on the upper externally-threaded body segment 12 is disposed on the upper externally-threaded body segment 12 in a manner that thread 12a aligns with (or matches) thread 14a on the lower externally-threaded body segment 12 when the expandable screw 10 is in the collapsed state.

Figure 4:
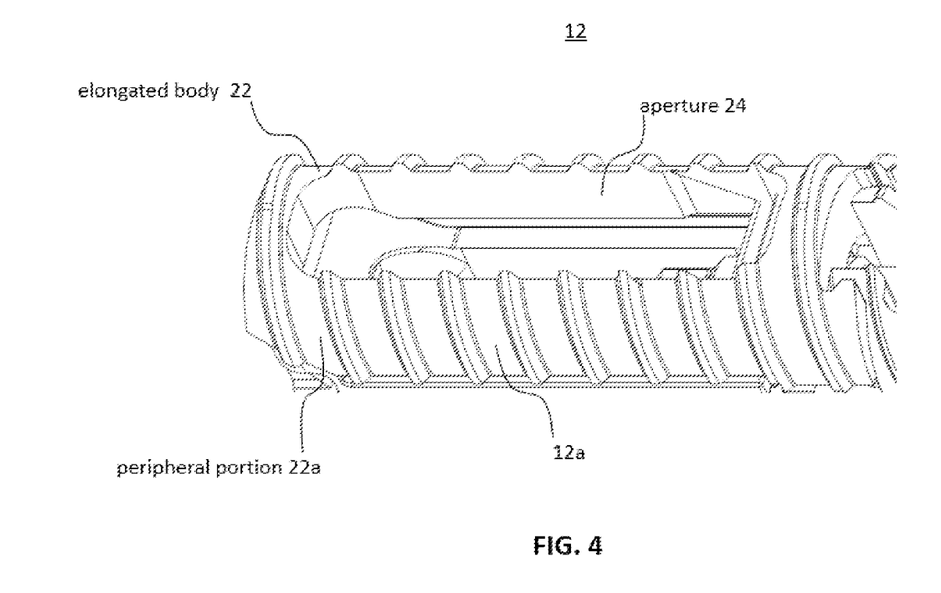
FIG. 4 is a perspective view of a threaded segment of the expandable screw of FIG. 1.

As seen in FIG. 4, upper externally-threaded body segment 12 can comprise an elongated body 22 having an aperture 24 which can extend in longitudinal and transverse directions of the elongated body 22. The aperture may be used for graft filling. Further, as seen in FIG. 4, the threads 12a, 14a can be disposed on outer peripheral sections 22a of elongated body 22. This thread arrangement is likewise applicable to the lower externally-threaded body segment 14. As also seen in FIG. 4, upper externally-threaded body segment 12 can comprise a cylindrical shell or be formed in a cylindrical shape. This shell configuration is likewise applicable to the lower externally-threaded body segment 14.

The Expansion Member

Expansion Member 16 in one embodiment can include a wedge member 18 connecting the upper externally-threaded body segment 12 to the lower externally-threaded body segment 14, a nose member 20 having a distal end and a proximal end opposite the distal end, the nose member 20 slidably connected to the upper externally-threaded body segment 12 and the lower externally-threaded body segment 14, and an actuator 33 disposed between the nose member 20 and the wedge member 18, for translation of the wedge member 18 along a longitudinal axis of the screw.

Figure 5:
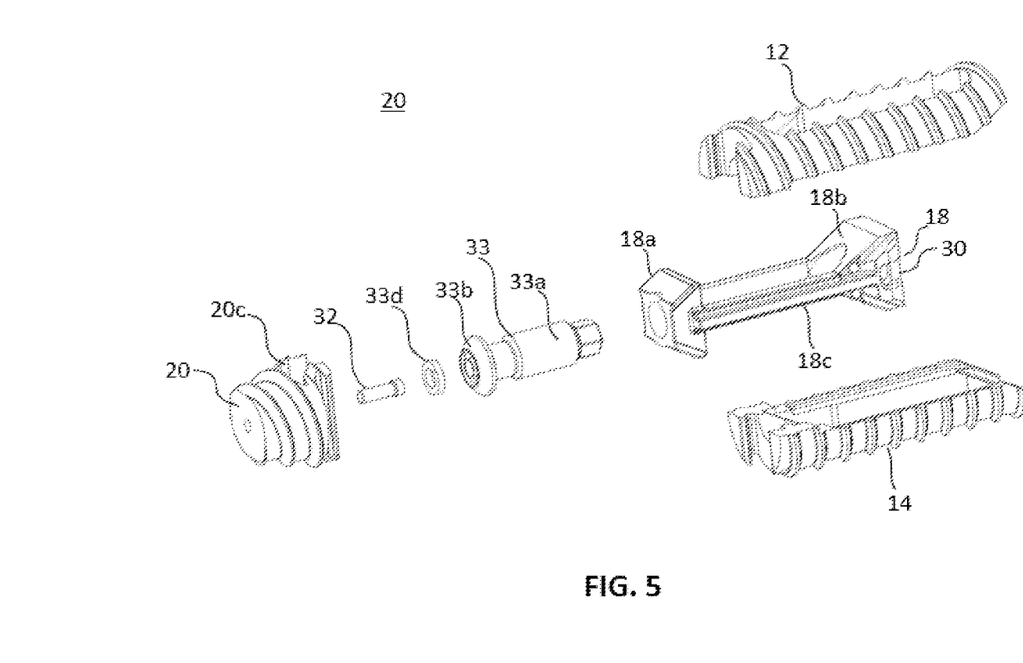
FIG. 5 is a schematic depiction of the individual components of the expandable screw, showing the relative positions of those components.

FIG. 5 is a schematic depiction of the individual components of the expandable screw 10 (including specific components of expansion member 16) showing the relative positions of those components. As evident from FIG. 5, actuator 33 is disposed between nose member 20 and wedge member 18. In one embodiment of the invention, the wedge member 18 comprises a first wedge 18a and a second wedge 18b connected together by one or more rails 18c. With reference to FIG. 5, nose member 20 connects to pin 32. Pin 32 retains the head of actuator 33 during expansion of screw 10 and positions the nose member 20 relative to the actuator 33.

In one embodiment, screw 10 expands by utilizing actuator 33 which is connected by a threaded connection to wedge member 18, which contains for example a pair of wedges 18a, 18b. When rotated, actuator 33 pulls the wedges (as a set) closer to the nose member 20 of and, in turn, drives the upper externally-threaded body segment 12 and the lower externally-threaded body segment 14 away from each other and away from the centerline of screw 10. In other words, with actuator 33 being threadably connected to wedge member 18, rotating actuator 33 translates the wedge member 18 along the longitudinal axis of screw 10. Actuator 33 in one embodiment has a threaded outside surface 33a with a head 33b of the actuator, opposite the wedge member 18, closer to the nose member 20 than to the posterior of screw 10. In one embodiment, actuator 33 and wedge member 18 have respectively male and female threads to thereby advance wedge member 18 when the actuator 33 is turned.

In one embodiment, actuator 33 is connected (e.g., by dovetail and groove construction) one side to nose member 20 and is connected (e.g., by dovetail and groove construction) on another side to wedge member 18. Translation of the wedge member 18 (for example along the longitudinal axis) in one embodiment displaces the upper externally-threaded body segment 12 from the lower externally-threaded body segment 14, and thereby expands the upper externally-threaded body segment 12 away from the lower externally-threaded body segment 14. Actuator can threadably connected to the wedge member such that rotating the actuator 33 translates the wedge member 18 along the longitudinal axis.

In one embodiment of the invention, actuator 33 is disposed closer to the nose member 20 than to a posterior of the screw 10. In general, the inventive screw expands by utilizing actuator 33 which is connected by a threaded connection to wedge member 18, which contains for example a pair of wedges 18a, 18b. When rotated, actuator 33 pulls the wedges (as a set) closer to the nose member 20 of screw 10 and, in turn, drives the upper externally-threaded body segment 12 and the lower externally-threaded body segment 14 away from the centerline of screw 10. In other words, with actuator 33 being threadably connected to wedge member 18, rotating actuator 33 translates the wedge member 18 along the longitudinal axis of screw 10. Actuator 33 in one embodiment has a threaded outside surface 33a with a head 33b of the actuator, opposite the wedge member 18, closer to the nose member 20 than to the posterior of screw 10. In one embodiment, actuator 33 and wedge member 18 have respectively male and female threads to thereby advance wedge member 18 when the actuator 33 is turned.

Figure 6:
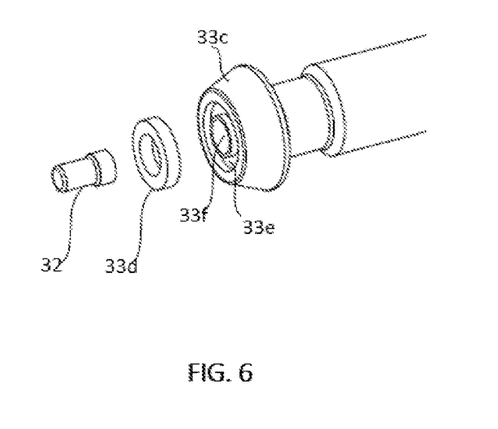
FIG. 6 is a schematic depicting an expanded view of a pin and actuator configuration for the expandable screw of FIG. 1.

FIG. 6 is an expanded view of the head 33b of the actuator 33 having a flange 33c which retains washer 33d into recess 33e. Washer 33d can be made from similar or dissimilar materials as the actuator, and in one example, washer 33d is made from polyetheretherketone (PEEK). Washer 33d is merely one example of a frictional bearing that provides a frictional force retarding movement of the upper externally-threaded body segment 12 and the lower externally-threaded body segment 14. As shown in FIG. 6, pin 32 fits into a reception hole 33f disposed on a central axis of the actuator 33. While the circular and symmetric geometry shown in FIG. 6 is preferred, the washer and its recess need not be circular and split washers and spacers could be placed on the flange in asymmetric patterns.

Regardless of the material that washer 33d is made of, washer 33d serves multiple purposes in the present invention. In one embodiment, compression of washer 33d in the interface between nose member 20 and actuator 33 provides friction. This friction helps keep the parts centered and prevents binding of the components during expansion/contraction. The friction also provides additional resistance to post operation collapse of the cage.

During assembly, pin 32 is pressed into the nose member 20 with a portion of pin 32 extending beyond the distal end of nose member 20. The upper externally-threaded body segment 12 and the lower externally-threaded body segment 14 are coupled to wedge member 18 along respective dovetails and dovetail groove with full engagement into a collapsed or non-expanded state. Actuator 33 is threaded into the wedge member 18. The head position of actuator 33 is adjusted so that it is aligned with the mating slot in nose member 20, while the vertical dovetails of the endplates are aligned with their mating dovetail grooves in nose member 20. Next, washer 33d is placed in recess 33e on flange 33c of the actuator. Then, the head of actuator 33 (with washer 33d in place) is slid into groove 20c of nose member 20, compressing washer 33d in the process to provide the friction noted above. Once the nose member 20 is close to alignment, pin 32 is pushed through an opening in the washer 33d into reception hole 33f of actuator 33. The part of pin 32 which formerly was protruding from the distal tip of nose member 20 is now flush with the distal tip of nose member 20.

In one embodiment of the invention (as described in U.S. Ser. No. 17/235,587), the frictional bearing can be a wave spring applying an axial force on the head of the actuator. In another embodiment of the invention, the frictional bearing can be a spring loaded cap to apply an axial force on the head of the actuator. In still another embodiment, the frictional bearing can be a PEEK pellet (or pin) inserted in the nose piece and oriented to interfere with the head of the actuator, and thereby apply an axial force on the head of the actuator.

Figure 7:
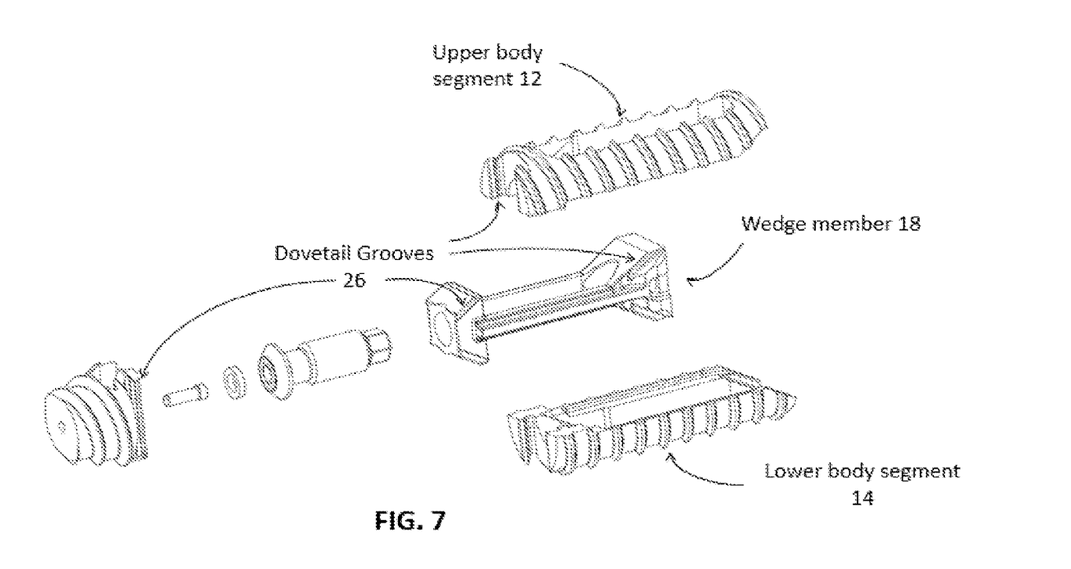
FIG. 7 is a schematic depicting a dovetail configuration for the expandable screw of FIG. 1.

FIG. 7 is a schematic depiction of the individual components of the expandable screw 10 with attention on the dovetail groove assembly construction. As seen in FIG. 7, nose member 20 uses dovetail grooves 26 to slidably connect and guide expansion of the body segments 12, 14 to wedge member 18, and restrain any anterior-posterior movement of the upper externally-threaded body segment 12 relative to the lower externally-threaded body segment 14. Moreover, in one embodiment, dovetail grooves 26 on the wedge member 18 hold and slidably connect the body segments 12, 14 to the wedge member 18. In another embodiment, dovetail grooves hold and slidably connect the upper externally-threaded body segment 12 and the lower externally-threaded body segment 14 to the nose member 20.

In still another embodiment, a series of dovetail grooves 26 connect individual components such as the nose member 20, the body segment 12, the wedge member 18 and the body segment 14 to each other so as to hold these components together as an expandable assembly. For example, a set of dovetail grooves on the first wedge 18a and the second wedge 18b slidably connect the wedge member 18 to the body segment 12 and body segment 14. Additionally, a first set of dovetail grooves 26 on the nose member 20 fix the nose member 20 to the upper externally-threaded body segment 12 and the lower externally-threaded body segment 14, while a second set of dovetail grooves 26 on the wedge member 18 fixes the upper externally-threaded body segment 12 and the lower externally-threaded body segment 14 to the wedge member 18.

Figure 8A:
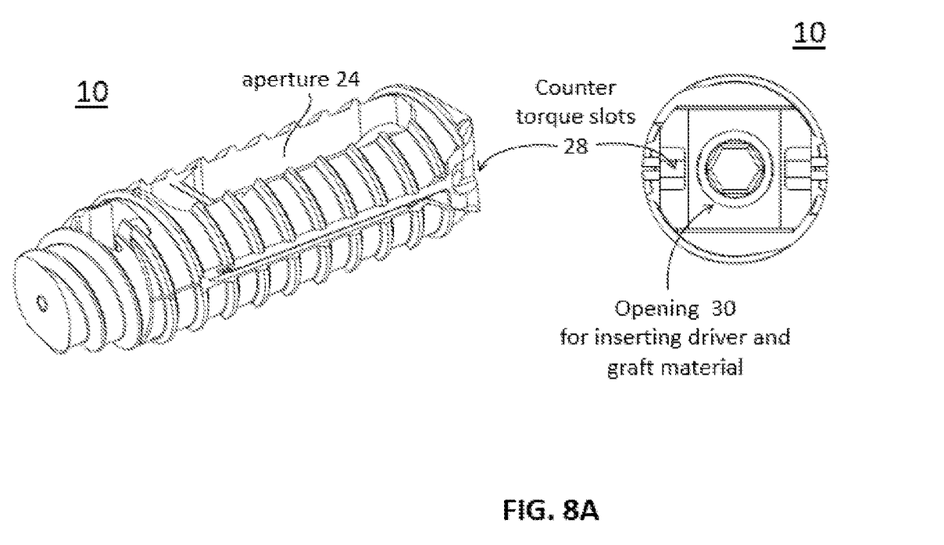
FIG. 8A is a schematic depicting counter torque slots of the expandable screw.

FIG. 8A is a schematic depicting counter torque slots 28 of screw 10 and an opening 30 in the posterior end of expandable screw 10. In one embodiment, opening 30 comprises a through hole in the posterior wedge member that opens into aperture 24. The counter torque slots 28 permit an entirety of expandable screw 10 to be rotated. The counter torque slots 28 may also hold against rotation when the actuation 33 is being turned. For example, the counter torque slots 28 can stabilize expandable screw 10 against the torque being applied by actuator 33 during expansion. The opening 30 grants access for the driver to the actuator. The opening 30 also represents a hole for insertion of bone graft material. In another embodiment of the invention, a through-hole in an end of wedge member 18, and a spacing between the rails 18c comprise a passageway for an insertion tool to connect to and turn actuator 33, and a passageway for bone graft material insertion. In one embodiment, the inclusion of aperture 24 and opening 30 in expandable screw 10 permits the bone graft material to be inserted through either or both of these passageways and contact the bone adjacent to body segments 12 and 14 and thereby promote bone growth inside the expandable screw 10.

Figure 8B:
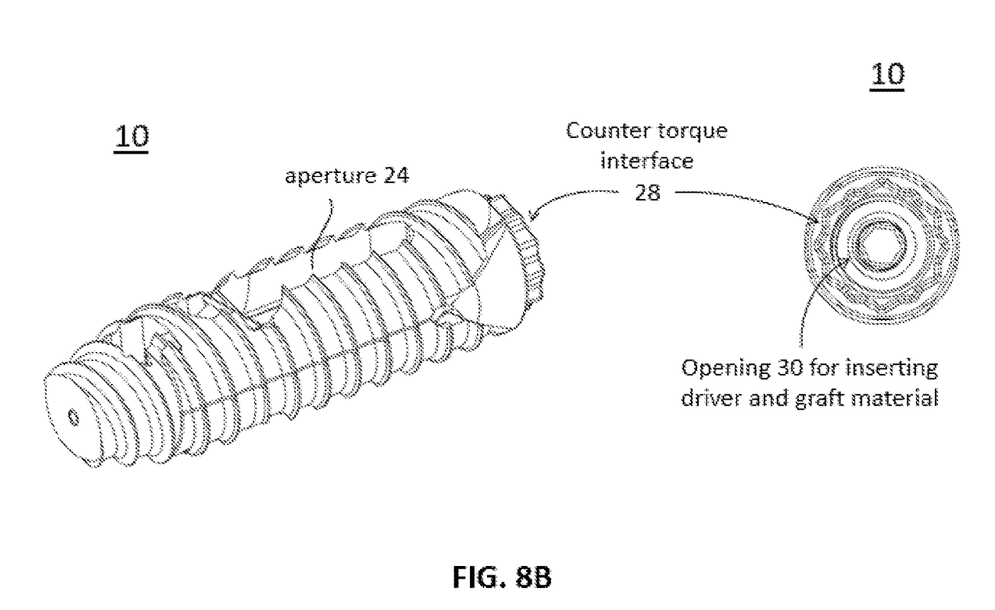
FIG. 8B is an alternative to the configuration of FIG. 8A.

FIG. 8B is an alternative to the configuration of FIG. 8A in which in FIG. 8B a twelve-point or "double hex" interface 28a is used. The double hex interface 28a offers a more robust option for advancing the entirety of the implant into bone as well as providing the counter torque for expansion.

In one embodiment of the invention, there is provided a system for orthopedic insertion and expansion of an expandable screw into a bone segment of a patient. This system can utilize a) any of the expandable screws described above; and b) an insertion tool which turns an actuator (as described above) and thereby expands the screw. For example, actuator 33 described above can be rotated by a T-7 hexalobular driver or actuator 33 can be rotated by a hexagonal socket driver. This system for orthopedic insertion and expansion of expandable screw 10 can utilize a bone graft inserter, which may be cannulated. In one embodiment, the above-noted T-7 driver or the hexagonal socket driver is placed through the center of the bone graft inserter and engages the actuator. Bone graft material is then pushed through the inserter after screw 10 has been expanded.

The expandable screws of the present invention are not limited to the type of material that the screw is made of. The screws of this invention can be made of any material appropriate for human implantation and having the mechanical properties sufficient to be utilized for the intended purpose of spinal fusion, including various metals such as cobalt chrome, stainless steel or titanium including its alloys, various plastics including those which are bio-absorbable, and various ceramics or combination sufficient for the intended purpose. Further, the screws of this invention may be made of a solid material, a mesh-like material, a porous material and may comprise, wholly or in part, materials capable of directly participating in the spinal fusion process, or be loaded with, composed of, treated of or coated with chemical substances such as bone, morphogenic proteins, hydroxyapatite in any of its forms, and osteogenic proteins, to make them bioactive for the purpose of stimulating spinal fusion. The screws of this invention may be wholly or in part bioabsorbable. Other materials for the expandable screw besides those specifically listed above can be used. In one embodiment, the materials of the expandable screw can be sterilized either at the time of manufacturing and/or at the time of insertion into a patient. In one embodiment, the surface finish of the expandable screw permit chemicals or steam sterilizing agents to penetrate the components of the screw and sterilize biological material on the surfaces.

This invention is also not limited to the methods by which the screws are made. The individual components can be machined from solid stock pieces. Molding can be used to make the individual components. In this case, machining to final dimensions may or may not be in order. The surfaces once properly dimensioned can be coated with a variety of biocompatible coatings and/or surface treatments. Various coatings include for example calcium phosphate ceramics, such as tricalcium phosphate (TCP) and hydroxyapatite (HA), and hydroxyapatite (a naturally occurring material in bone). Moreover, screw 10 may be treated to promote fusion of the screw to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces of the screw.

Operation of Expandable Screw

Figure 9:
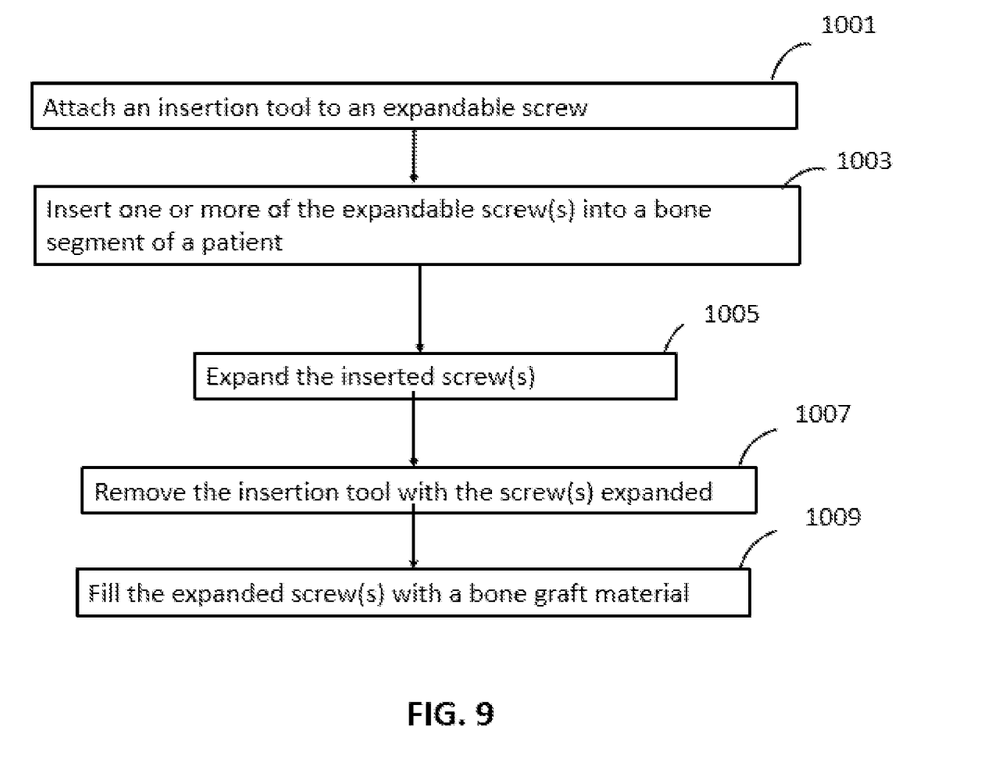
FIG. 9 is a flowchart depicting a method of the invention for orthopedic insertion and expansion of an expandable screw into a bone segment of a patient.

In one embodiment of the invention, there is provided a method for orthopedic insertion and expansion of an expandable screw into a bone segment of a patient. FIG. 9 is a flowchart depicting this method. This method at 1001 attaches an insertion tool to any of the expandable screws described above. At 1003, the method inserts one (or more) of the expandable screws into to a bone segment of a patient; and at 1005 expands the expandable screw.

After the expandable screw has been expanded, at 1007, the insertion tool may be removed (e.g., may be pulled from through hole 30 in the posterior end of screw 20. At 1009, bone graft material may then be inserted into the expanded screw filling the graft in the expanded screw in situ. Insertion of bone graft material may promote increased fusion.

This invention is not limited to a specific type of bone graft material. In general, a variety of bone graft materials are known and suitable for this invention. These typically comprise calcium phosphate-based or gel-based materials. Polymer-based bone graft substitutes containing (or not containing) collagen can be used. Ceramic bone graft substitutes can be used. In one embodiment, the implantable bone graft material comprises a composite of a ceramic and a polymer. The ceramic and the polymer can be present at a weight ratio ranging from about 10:1 ceramic to polymer to about 2:1 ceramic to polymer. Alternatively, the weight ratio of the ceramic to the polymer can range from about 2:1 (about 66% ceramic to about 33% polymer), from about 3:1 (about 75% ceramic to about 25% polymer), from about 4:1 (about 80% ceramic to about 20% polymer), from about 9:1 (about 90% ceramic to about 10% polymer), from about 10:1 (about 99% ceramic to about 1% polymer). Other bone graft materials besides those specifically listed above can be used.

In some embodiments, any of the screws and instruments described above (such as the insertion tool) can be used with additional screws, implants, and instruments. In some embodiments, the implants and instruments can be used with stabilization members, such as plates, screws, and rods.

STATEMENTS OF THE INVENTION

The following are non-limiting statements of the invention describing various aspects of the invention. Non-limiting reference is made below to the enumerated elements in the drawings. However, these statements (and the claims to follow) are not limited to the embodiments depicted in the drawings, Statement 1. An expandable screw 10 for orthopedic insertion and expansion between a collapsed state and an expanded state, comprising: an upper externally-threaded body segment 12; a lower externally-threaded body segment 14 opposite the upper external thread segments 12; and an expansion member 16 extending along a longitudinal axis thereof, connecting the upper externally-threaded body segment 12 to the lower externally-threaded body segment 14, and configured during the expansion between the collapsed state and the expanded state to separate the upper externally-threaded body segment 12 from the lower externally-threaded body segment 14.

Statement 2. The screw of statement 1, wherein the expansion member 16 expands the upper externally-threaded body segment 12 from the lower externally-threaded body segment 14 in a single expansion direction.

Statement 3. The screw of any one or more of the above statements, wherein the expansion member 16 expands the upper externally-threaded body segment 12 from the lower externally-threaded body segment 14 in a single expansion direction without a radial deflection of the upper externally-threaded body segment 12 from the lower externally-threaded body segment 14.

Statement 4. The screw of any one or more of the above statements, wherein the expansion member 16 expands the upper externally-threaded body segment 12 from the lower externally-threaded body segment 14 while the upper externally-threaded body segment 12 and the lower externally-threaded body segment 14 remains in a fixed (or substantially fixed) orientation relative to each other.

Statement 5. The screw of any one or more of the above statements, wherein the upper externally-threaded body segment 12 and the lower externally-threaded body segment 14 comprise threads for securing the screw to a bone segment of a patient.

Statement 6. The screw of any one or more of the above statements, wherein at least one of the upper externally-threaded body segment 12 and the lower externally-threaded body segment 14 comprises an elongated body 22 having an aperture (which extend in longitudinal and traverse directions of the elongated body).

Statement 7. The screw of statement 6, wherein at least one of the upper externally-threaded body segment 12 and the lower externally-threaded body segment 14 comprise threads for securing the screw to a bone segment in a patient, and the threads are disposed on outer peripheral sections of the upper externally-threaded body segment 12 and the lower externally-threaded body segment 14.

Statement 8. The screw of statement 6, wherein at least one of the outer peripheral sections of one of the upper externally-threaded body segment 12 and the lower externally-threaded body segment 14 comprises a cylindrical shell.

Statement 9. The screw of any one or more of the above statements, wherein at least one of the upper externally-threaded body segment 12 and the lower externally-threaded body segment 14 comprises an elongated body 22 having a cylindrical shape.

Statement 10. The screw of statement 9, further comprising threads disposed on the elongated body for securing the screw to a bone segment in a patient.

Statement 11. The screw of any one or more of the above statements, wherein the expansion member 16 comprises: a wedge member 18 connecting the upper externally-threaded body segment 12 to the lower externally-threaded body segment 14; a nose member 20 having a distal end and a proximal end opposite the distal end, the nose member 20 slidably connected to the upper externally-threaded body segment 12 and the lower externally-threaded body segment 14; and an actuator 33 disposed between the nose member 20 and the wedge member 18, for translation of the wedge member 18 along a longitudinal axis of the screw.

Statement 12. The screw of statement 11, wherein the actuator 33 on a first side slidably is connected the nose member 20 and on a second side is connected to the wedge member 18; and translation of the wedge member 18 relative to the upper externally-threaded body segment 12 and the lower externally-threaded body segment 14 (e.g., along the longitudinal axis of the expandable screw) displaces the upper externally-threaded body segment 12 and the lower externally-threaded body segment 14 away from each other, thereby expanding the upper externally-threaded body segment 12 away from the lower externally-threaded body segment 14.

Statement 13. The screw of statements 11 or 12, wherein the expansion member 16 further comprises: a pin coupling the actuator 33 to the nose member 20.

Statement 14. The screw of statement 13, wherein the pin maintains a position of the nose member 20 relative to the actuator 33 once the expandable screw has been assembled.

Statement 15. The screw of any one or more of statements 11-14, wherein the actuator 33 is threadably connected to the wedge member 18 such that rotating the actuator 33 translates the wedge member 18 along the longitudinal axis.

Statement 16. The screw of any one or more of statements 11-15, wherein the wedge member 18 comprises a first wedge and a second wedge connected together by a rail.

Statement 17. The screw of any one or more of statements 11-16, wherein dovetail grooves on the wedge member 18 hold and slidably connect the upper externally-threaded body segment 12 and the lower externally-threaded body segment 14 to the wedge member 18.

Statement 18. The screw of any one or more of statements 11-17, wherein dovetail grooves on the nose member 20 hold and slidably connect the upper externally-threaded body segment 12 and the lower externally-threaded body segment 14 to the nose member.

Statement 19. The screw of any one or more of statements 11-18, wherein the dovetail grooves are disposed on a posterior side of the nose member.

Statement 20. The screw of any one of statements 11-19, wherein a posterior of the actuator is configured to connect with an insertion tool for insertion of the implant between vertebra.

Statement 21. The screw of claim 1 any one of statements 11-21, wherein the actuator is disposed closer to the nose member than to a posterior end of the screw.

Statement 22. The screw of any one or more of statements 11-22, wherein the actuator by turning advances the wedge member 18 toward the nose member to expand the screw.

Statement 23. The screw of any one or more of statements 11-22, wherein the actuator and the wedge member have respectively male and female threads to thereby advance the wedge member when the actuator is turned.

Statement 24. The screw of any one or more of statements 11-23, further comprising: a first set of dovetail grooves on the nose member which fix the nose member to the upper externally-threaded body segment 12 and the lower externally-threaded body segment 14, and a second set of dovetail grooves on the wedge member 18 which fix the upper externally-threaded body segment 12 and the lower externally-threaded body segment 14 to the wedge member 18.

Statement 25. The screw of any one or more of statements 11-24, wherein the wedge member 18 comprises a first wedge and a second wedge connected together by a pair of rails, and a first through-hole in the first wedge, a second through-hole in the second wedge, and a spacing between the rails comprise a passageway for an insertion tool to connect to and turn the actuator.

Statement 26. The screw of any one or more of statements 11-26, wherein the wedge member 18 comprises a first wedge and a second wedge connected together by a pair of rails, and the second wedge at a posterior end has counter torque slots by which an entirety of the screw is rotatable.

Statement 27. The screw of any one or more of statements 11-26, wherein the nose member 20 slidably connects to the upper externally-threaded body segment 12 and the lower externally-threaded body segment 14 by a set of dovetail groove on an external surface of the nose member.

Statement 28. The screw of any one or more of statements 11-27, wherein the wedge member 18 comprises a first wedge and a second wedge, and a set of dovetail grooves on the first wedge and the second wedge slidably connect the wedge member to the upper externally-threaded body segment 12.

Statement 29. The screw of any one or more of statements 11-28, wherein the set of dovetail grooves on the first wedge and the second wedge slidably connect the wedge member 18 to the lower externally-threaded body segment 14.

Statement 30. The screw of any one or more of the above statements, wherein, upon expansion to the expanded state, windows for bone graft filling exist a) between the upper externally-threaded body segment 12 and the lower externally-threaded body segment 14 and b) in apertures 24 forming elongated openings on both the upper externally-threaded body segment 12 and the lower externally-threaded body segment 14.

Statement 31. A system including the expandable screw of claim 1 wherein the screw is for orthopedic insertion and expansion into a bone segment of a patient, and the system comprising any one or more of the above expandable screws in statements 1-30 and further comprising an insertion tool which is configured to connect to the expandable screw for actuation and expansion of the expandable screw.

Statement 32. A method for utilizing any one or more of the above expandable screws in statements 1-30 for orthopedic insertion and expansion of the expandable screw into a bone segment of a patient, the method comprising:
 inserting the expandable screw into the bone segment of the patient; and
 expanding the expandable screw.

Numerous modifications and variations of the present invention are possible in light of the above teachings. It is therefore to be understood that within the scope of the appended claims, the invention may be practiced otherwise than as specifically described herein.

The invention claimed is:

1. An expandable screw for orthopedic insertion and expansion between a collapsed state and an expanded state, comprising:
 an upper externally-threaded body segment;
 a lower externally-threaded body segment opposite the upper externally-threaded body segment; and
 an expansion member extending along a longitudinal axis thereof, connecting the upper externally-threaded body segment to the lower externally-threaded body segment, and configured, during the expansion between the collapsed state and the expanded state, to separate the upper externally-threaded body segment from the lower externally-threaded body segment, the expansion member comprising a wedge member, an actuator, and a nose member having a distal end and a proximal end opposite the distal end, the nose member slidably connected to the upper externally-threaded body segment and the lower externally-threaded body segment, extending beyond the upper externally-threaded body segment and the lower externally-threaded body segment, and the nose member having external threads for engaging a bone segment of a patient, the external threads extending from the proximal end toward the distal end.

2. The screw of claim 1, wherein the expansion member expands the upper externally-threaded body segment from the lower externally-threaded body segment in a single expansion direction.

3. The screw of claim 1, wherein the expansion member expands the upper externally-threaded body segment from the lower externally-threaded body segment in a single expansion direction without a radial deflection of the upper externally-threaded body segment from the lower externally-threaded body segment.

4. The screw of claim 1, wherein the expansion member expands the upper externally-threaded body segment from the lower externally-threaded body segment while the upper externally-threaded body segment and the lower externally-threaded body segment remain in a fixed orientation relative to each other.

5. The screw of claim 1, wherein threads of the upper externally-threaded body segment and the lower externally-threaded body segment are each configured to secure the screw to a bone segment of a patient.

6. The screw of claim 1, wherein at least one of the upper externally-threaded body segment and the lower externally-threaded body segment comprises an elongated body having an aperture.

7. The screw of claim 1, wherein threads of the upper externally-threaded body segment and the lower externally-threaded body segment are each configured to secure the screw to a bone segment in a patient, and wherein the threads are disposed on outer peripheral sections of the upper externally-threaded body segment and the lower externally-threaded body segment.

8. An expandable screw for orthopedic insertion and expansion between a collapsed state and an expanded state, comprising:
 an upper externally-threaded body segment;
 a lower externally-threaded body segment opposite the upper externally-threaded body segment; and
 an expansion member extending along a longitudinal axis thereof, connecting the upper externally-threaded body segment to the lower externally-threaded body segment, and configured, during the expansion between the collapsed state and the expanded state, to separate the upper externally-threaded body segment from the lower externally-threaded body segment, the expansion member comprising a wedge member, an actuator, and an externally threaded nose member having a distal end and a proximal end opposite the distal end, the nose member slidably connected to the upper externally-threaded body segment and the lower externally-threaded body segment and extending distally beyond the upper externally-threaded body segment and the lower externally-threaded body segment;
 wherein threads of the upper externally-threaded body segment and the lower externally-threaded body segment are each configured to secure the screw to a bone segment in a patient,
 wherein the threads are disposed on outer peripheral sections of the upper externally-threaded body segment and the lower externally-threaded body segment, and wherein at least one of the outer peripheral sections of one of the upper externally-threaded body segment and the lower externally-threaded body segment comprises a partially cylindrical shell.

9. The screw of claim 1, wherein at least one of the upper externally-threaded body segment and the lower externally-threaded body segment comprises an elongated body having a partially cylindrical shape.

10. The screw of claim 9, wherein the upper externally-threaded body segment, the lower externally-threaded body segment, and the external threads of the nose member are configured to secure the screw to the bone segment in the patient.

11. The screw of claim 1, wherein the wedge member connects the upper externally-threaded body segment to the lower externally-threaded body segment; and wherein the actuator is disposed between the nose member and the wedge member, for translation of the wedge member along a longitudinal axis of the screw.

12. An expandable screw for orthopedic insertion and expansion between a collapsed state and an expanded state, comprising:
an upper externally-threaded body segment;
a lower externally-threaded body segment opposite the upper externally-threaded body segment; and
an expansion member extending along a longitudinal axis thereof, connecting the upper externally-threaded body segment to the lower externally-threaded body segment, and configured, during the expansion between the collapsed state and the expanded state, to separate the upper externally-threaded body segment from the lower externally-threaded body segment,
wherein the expansion member comprises:
a wedge member connecting the upper externally-threaded body segment to the lower externally-threaded body segment;
a nose member having a distal end and a proximal end opposite the distal end, the nose member slidably connected to the upper externally-threaded body segment and the lower externally-threaded body segment; and
an actuator disposed between the nose member and the wedge member, for translation of the wedge member along a longitudinal axis of the screw,
wherein the actuator, on a first side, is slidably connected to the nose member and, on a second side, is connected to the wedge member; and
wherein translation of the wedge member relative to the upper externally-threaded body segment and the lower externally-threaded body segment displaces the upper externally-threaded body segment and the lower externally-threaded body segment away from each other, thereby expanding the upper externally-threaded body segment away from the lower externally-threaded body segment.

13. The screw of claim 11, wherein the expansion member further comprises: a pin coupling the actuator to the nose member.

14. The screw of claim 13, wherein the pin maintains a position of the nose member relative to the actuator once the screw has been assembled.

15. The screw of claim 11, wherein the actuator is threadably connected to the wedge member such that rotating the actuator translates the wedge member along the longitudinal axis.

16. The screw of claim 11, wherein the wedge member comprises a first wedge and a second wedge connected together by a rail.

17. The screw of claim 11, wherein dovetail grooves on the wedge member hold and slidably connect the upper externally-threaded body segment and the lower externally-threaded body segment to the wedge member.

18. The screw of claim 1, wherein, in the expanded state, windows for bone graft filling are disposed between the upper externally-threaded body segment and the lower externally-threaded body segment.

19. A system comprising the expandable screw of claim 1 and an insertion tool configured to connect to the expandable screw for actuation and expansion of the expandable screw.

20. A method for utilizing an expandable screw for orthopedic insertion and expansion into a bone segment of a patient, the method comprising:
inserting the expandable screw of claim 1 into the bone segment of the patient; and expanding the expandable screw.

21. The screw of claim 1, wherein, in the expanded state, elongated openings between the upper externally-threaded body segment and the lower externally-threaded body segment form windows for bone graft filling.

* * * * *